United States Patent [19]

Lehrman et al.

[11] Patent Number: 5,663,305
[45] Date of Patent: Sep. 2, 1997

[54] SOMATOTROPIN ANALOGS

[75] Inventors: Sherwood Russ Lehrman; Henry A. Havel; Jody L. Tuls; Scott M. Plaisted, all of Kalamazoo, Mich.; David N. Brems, Indianapolis, Ind.

[73] Assignee: The Upjohn Company, Kalamazoo, Mich.

[21] Appl. No.: 365,996

[22] Filed: Dec. 29, 1994

Related U.S. Application Data

[63] Continuation of Ser. No. 82,802, Jun. 24, 1993, abandoned, which is a continuation of Ser. No. 778,202, Dec. 13, 1991, abandoned, which is a continuation-in-part of Ser. No. 377,926, filed as PCT/US90/03550, Jun. 27, 1990, abandoned.

[51] Int. Cl.$^6$ .......................... C07K 14/61; A61K 38/27; C12P 21/06
[52] U.S. Cl. .......................... 530/399; 435/69.4
[58] Field of Search .................. 530/399; 514/2; 435/69.4

[56] References Cited

FOREIGN PATENT DOCUMENTS

| 0089666 | 9/1983 | European Pat. Off. . |
|---|---|---|
| 0193515 | 9/1986 | European Pat. Off. . |
| 0263206 | 4/1988 | European Pat. Off. . |

OTHER PUBLICATIONS

N.E. Down, et al., Can. J. Fish. Aquat. Sci. vol. 46, (1989) pp. 178–83, "A Potent Analog of Recombinant Bovine Somatotropin Accelerates Growth in Juvenile Coho Salmon (*Oncorhynchus kisutch*)".

Levitt et al. Biochemistry 17(20): 4277 1978.

Brems et al Biochemistry 26:7774 1987.

Brems et al. PNAS 85:3367 1988.

Watahiki et al 1989 J Biol. Chem. 264:312–316.

*Primary Examiner*—Robert A. Wax
*Assistant Examiner*—K. Cochrane Carlson
*Attorney, Agent, or Firm*—James D. Darnley, Jr.; Paul J. Koivuniemi; Gregory W. Steele

[57] ABSTRACT

The present invention provides analogs of animal somatotropins particularly with changes in the amino acids between residue 96 to 133 which are changed to reduce hydrophobicity or helical stability.

12 Claims, 2 Drawing Sheets

FIG. 1A ala phe pro ala met ser leu ser gly leu
                                      20
phe ala asn ala val leu arg ala gln his leu his gln leu ala ala asp thr phe lys
                                      40
glu phe glu arg thr tyr ile pro glu gly gln arg tyr ser ile gln asn thr gln val
                                      60
ala phe cys phe ser glu thr ile pro ala pro thr gly lys asn glu ala gln gln lys
                                      80
ser asp leu glu leu leu arg ile ser leu leu leu ile gln ser trp leu gly pro leu
                                     100
gln phe leu ser arg val phe thr asn ser

FIG. 1B leu val phe gly thr ser asp arg val tyr
                                        120
glu lys leu lys asp leu glu glu gly ile leu ala leu met arg glu leu glu asp gly
                                        140
thr pro arg ala gly gln ile leu lys gln thr tyr asp lys phe asp thr asn met arg
                                        160
ser asp asp ala leu leu lys asn tyr gly leu leu ser cys phe arg lys asp leu his
                                        180
lys thr glu thr tyr leu arg val met lys
                                        190
cys arg arg phe gly glu ala ser cys ala phe

1

SOMATOTROPIN ANALOGS

This application is a file wrapper continuation of U.S. Ser. No. 08/082,802, filed Jun. 24, 1993, now abandoned, which is a file wrapper continuation of U.S. Ser. No. 07/778,202, filed Dec. 13, 1991, abandoned; which is a continuation-in-part of the National Stage of International Application PCT/US90/03550, which is a continuation-in-part of U.S. Ser. No. 07/377,926, filed Jul. 10, 1989, now abandoned.

FIELD OF INVENTION

This invention describes novel mammalian somatotropins or growth hormones that contain changes in the primary structure between residues 96 to 133. These changes reduce hydrophobicity or helical stability of the somatotropin molecule.

BACKGROUND OF THE INVENTION

Somatotropins were originally discovered in pituitary gland extracts from various animals. Mammalian somatotropins are conserved molecules resulting in similar tertiary structure.

Somatotropins, including bovine somatotropins (bSt), are globular proteins comprising a single chain of about 200 amino acids with two intramolecular disulfide bonds. bSt is a growth hormone which has been extensively studied (Paladini, A. C. et al., CRC Crit. Rev. Biochem. 15:25–56 (1983)). Specifically, bSt is a globular, single chain protein containing 191 amino acids and two intramolecular disulfide bonds. The molecular weight of bSt is about 22,000 daltons.

Natural bSt extracted from pituitary glands is heterogeneous. At least six major forms of the protein have been described. The longest form has 191 amino acid residues and the sequence alanylphenylaalanine at the $NH_2-$ terminus. The second form has 190 amino acid residues and phenylalanine at the $NH_2-$ terminus. The third form has 187 amino acid residues and methionine at the $NH_2-$ terminus. The remaining three forms of the bSt substitute valine for leucine at position 127. In addition to this heterogeneity, undefined heterogeneity of bovine somatotropin has also been described (Hart, I. C. et al., Biochem. J. 218:573–581 (1984); Wallace, M. and Dickson, H. B. F., Biochem. J. 100:593–600 (1965)). Undefined electrophoretic heterogeneity is seen when the native extracts are fractionated by anion exchange chromatography. It has been shown that the defined forms have different relative potency in bioassays. Also, it has been shown that other undefined species of bSt, when fractionated on ion exchange columns, have varying degrees of bioactivity in rat growth models (Hart, et al. and Wallace and Dickson, supra).

It is not known whether the undefined heterogeneity exhibiting biological variation is due to genetic variability, to in vivo post-translational modification, to differences in phosphorylation (Liberti, J. P. et al., Biochem. and Biophys. Res. Comm. 128:713–720, 1985), or to artifacts of isolation.

Bovine somatotropin produced by recombinant microorganisms (rbSt), or extracted from pituitary gland tissue, is important commercially. It increased lactation in dairy cattle and increases size and meat production in beef cattle. It is estimated that upwards to 20 mg per animal per day is needed to effect commercially acceptable improvements in production. Such a dosage will require efficient methods of administration. Improvements in the potency and stability of bSt such as described in this invention will be of benefit because of resulting reductions in the amount of drug administered to each animal per day.

Porcine somatotropin has the three-dimensional structure of a four-helical bundle protein (Abdel-Meguid, S. S., Sieh, H.-S., Smithe, W. W., Dayringer, H. E., Violand, B. N., and Bentle, L. A. (1987) Proc. Natl. Acad. Sci. USA, 84, 6434–6437). The native conformation removes many hydrophobic amino acid residues from the surface of the protein thereby increasing solubility. Hydrophobic amino acid residues (those that are least soluble in aqueous buffers) have been classified using the scale established by Eisenberg. When partially unfolded, these hydrophobic amino acids are exposed to the aqueous medium and protein precipitation may result. Precipitation of rbSt that is observed during its manufacture likely occurs partially through this mechanism. In addition, bSt produced as a heterologous protein in E. coli is initially found in an insoluble state that may also result from these mechanisms (World Patent WO 8700204 and U.S. Pat. No. 4,518,526). The insoluble form of bSt can be solubilized by addition of detergents or denaturing agents. Biological activation occurs following removal of these reagents under controlled conditions, allowing the native conformation to form (World Patent WO 8700204 and U.S. Pat. No. 4,518,526). Once the native conformation is attained, bSt is relatively soluble. In the process of further manufacturing, however, rbSt is again exposed to conditions that perturb the native conformation, frequently leading to precipitation. For example, interfacial denaturation of bSt solutions is commonly encountered and is accelerated by vortexing or vigorous shaking. As above, the resulting precipitate is biologically inactive and may cause undesirable immunological responses. In addition, rapid pH changes or heating to temperatures >75° can cause considerable precipitation of bSt (Burger, H. G., Edelhoch, H., and Condliffe, P. G. (1966) J. of Biol. Chem., 241, 449–457).

Previous equilibrium folding studies of bSt have identified a stable folding intermediate that forms on partial denaturation and aggregates at elevated protein concentrations (the terms aggregation and self-association, or simply association, are used here in the same manner) (Havel, H. A., Kauffman, E. W., Plaisted, S. M., and Brems, D. N. (1986) Biochemistry, 25, 6533–6538, and Brems, D. N., Plaisted, S. M., Kauffman, E. W., and Havel, H. A. (1986) biochemistry, 25, 6539–6543). This aggregated protein species is less soluble than the native or denatured conformations (Brems, Biochemistry 1988). Procedures have been developed to selectively precipitate and quantitate the aggregated intermediate. It has been shown that the aggregated intermediate is transiently populated during the kinetic refolding of bSt at elevated protein concentrations. If refolding is conducted in solutions that do not solubilize this protein species, the majority of bSt precipitates. If refolding is conducted in solutions that solubilize the aggregated intermediate, then native protein is quantitatively obtained (Brems, D. N., Plaisted, S. M., Dougherty, J. J. Jr., and Holzman, T. F. (1987) J. Biol. Chem., 262, 2590–2596).

Kinetic studies have led to the following model to describe bSt folding:

Scheme I

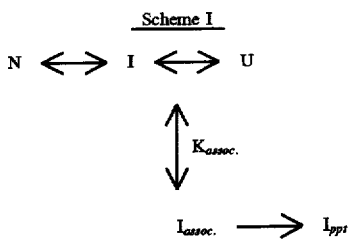

where, N=native rbSt, I=monomeric folding intermediate, $I_{assoc}$=associated intermediate, U=unfolded rbSt, $K_{assoc}$= equilibrium constant for self-association, and $I_{ppt}$= precipitated protein.

Convenient and selective methods that quantitate aggregated intermediate have been developed. For example, near UV circular dichroism (CD) of bSt, under conditions that lead to the formation of aggregation have a unique spectral band at 300 nm. (Havel, H. A., Kauffman, E. W., Plaisted, S. M., and Brems, D. N. (1986) Biochemistry, 25, 6533–6538). The aggregation alters the CD spectrum of the single tryptophan and results in this negative ellipticity. The presence of the aggregated intermediate also alters the equilibrium denaturation transitions (Havel, H. A., Kauffman, E. W., Plaisted, S. M., and Brems, D. N. (1986) Biochemistry, 25, 6533–6538, and Brems, D. N., Plaisted, S. M., Kauffman, E. W., and Havel, H. A. (1986) Biochemistry, 25, 6539–6543)). A region of bSt spanning residues 107 to 127 forms an amphiphilic α-helix and has been identified as a critical region that participates in the formation of the aggregation intermediate. By including an excess of fragment 109–133 or 96–133 to rbSt during refolding the formation of the associated intermediate is prevented and consequently no precipitate is formed (Brems, D. N., Plaisted, S. M., Kauffman, E. W., and Havel, H. A. (1986) Biochemistry, 25, 6539–6543). If Lys 112-rbSt (i.e., bSt with a lysine residue at position 112) is changed to a leucine residue (i.e., bSt with a leucine residue at position 112) by site-directed mutagenesis, then the hydrophobic portion of the amphiphilic helix is expanded, resulting in stabilization of the aggregated intermediate and which, therefore, undergoes more precipitation via the mechanism described above.

We have undertaken to solve these problems by designing analogs of bSt and pSt which self-associate, or aggregate, to a lesser extent that the parent proteins by synthesizing analogs that are less subject to aggregation because of reduced hydrophobicity while retaining or enhancing their biological activity. In addition, we have designed analogs that contain less α-helicity between residues 109 to 127, thereby reducing the potential of this region for hydrophobic interactions or partial denaturation.

INFORMATION DISCLOSURE

Analogs of bSt are known (see, for example, European patent applications 75,444, 103,395, and 193,515 and Nucleic Acid Res. 10(20):6487 (1982) and N. E. Down, et al., Can. J. Fish. Aquat. Sci., 46, pp. 178–83 (1989)).

G. Winter and A. R. Fersht, TIBS, 2, p. 115 (1984) review the alteration of enzyme activity by changing amino acid composition at key sequence locations.

P. Y. Chou and G. D. Fasman, Ann. Rev. Biochem., 47, pp. 251–76 (1978) and P. Y. Chou and G. D. Fasman, J. Mol. Biol., 115, pp. 135–75 (1977) refer to the use of amino acid sequences to predict the secondary of proteins. H. A. Havel et al., Biochemistry, 25, pp. 6533–38 (1986) and D. N. Brems, et al., Biochemistry, 25, pp. 6539–43 (1986) refer to the characterization of a self-associated species resulting from partial denaturation of rbSt at high concentration.

D. N. Brems, et al., Biochemistry, 26, pp. 7774–78 (1987) refer to self-association of bSt fragments consisting of amino acids 96–133 and 109–133.

D. N. Brems, Biochemistry, 27, pp. 4541–46 (1988) refers to the solubility of different folding conformers of bSt. At high concentrations, the self-associated rbSt readily precipitate following rapid dilution of denaturant. In addition, fragment 96–133 was shown to inhibit self-association and precipitation of rbSt.

D. N. Brems, et al., Proc. Natl. Acad. Sci. USA, 85, pp. 3367–71 (1988) refers to stabilization of the bSt associated folding intermediate by site-directed replacement of the 112 lysine residue of bSt with leucine. They explain that the increased stability of the associated intermediate and the increased helicity of the mutant peptide are due to increased hydrophobic interactions between this bSt region with other protein molecules.

None of these documents discloses or suggests the specific mammalian somatotropin analogs, and, in particular, bSt and pSt analogs, of the instant invention nor the use of such analogs to eliminate the self-association problem.

SUMMARY OF THE INVENTION

This invention describes analogs of somatotropins, particularly bSt and pSt that enhance bioactivity or lessen aggregation during processing, or both, by substituting single or multiple amino acid residues between amino acid residues 109 to 133 of native bSt or the related residues of other somatotropins. These analogs reduce hydrophobicity or the helical stability of this protein region, resulting in a lessening in the propensity of the partially denatured protein for aggregation and precipitation. Other changes that lead to decreased α-helical stability within this region but do not decrease hydrophobicity of the protein are included. These latter compounds form a smaller organized hydrophobic region, and therefore undergo reduced aggregation. Similar changes can be made in somatotropins from other animals, particularly mammals, including porcine, ovine, horse, rat, monkey, and human.

More specifically, and preferred, are those species of bSt-like compounds wherein the leucine located at amino acid residue 121 (Leu-121) is replaced with another amino acid residue including specifically glutamine (Gln-121) or in which arg-125 and glu-126 are replaced by glycine and arginine respectively.

More specifically, the animal somatotropin is selected from the group consisting of bovine, porcine, fish, ovine, horse, rat, monkey, and human somatotropins.

Even more specifically, the animal somatotropin is bovine or porcine somatotropin, specifically, bovine.

Other specifically claimed molecules include those selected from the group consisting of the following replacements (the corresponding positions can be determined by referring to FIGS. 1A and B):

Leu-113 replacements: Arg-113, Lys-113, Asp-113, Gln-113, Asn-113, Glu-113, His-113, Ser-113, Thr-113, Pro-113, Tyr-113, Gly-113, Ala-113, Met-113, Trp-113, Phe-113, Ile-113, Val-113, Leu-116 replacements: Arg-116, Lys-116, Asp-116, Gln-116, Asn-116, Glu-116, His-116, Ser-116, Thr-116, Pro-116, Tyr-116, Gly-116, Ala-116, Met-116, Trp-116, Phe-116, Ile-116, Val-116; Ile-120 replacements: Arg-120, Lys-120, Asp-120, Gln-120, Asn-120, Glu-120, His- 120, Ser-120, Thr-120, Pro-120; Leu-123 replacements: Arg-123, Lys-123, Asp-123, Gln-123, Asn-123, Glu-123, His-123, Ser-123, Thr-123, Pro-123, Tyr-123, Gly-123, Ala-123, Met-123, Trp-123, Phe-123, Ile-123, Val-123; Leu-127 replacements: Arg-127, Lys-127, Asp-127, Gln-127, Asn-127, Glu-127, His-127, Ser-127, Thr-127, Pro-127, Tyr-127, Gly-127, Ala-127, Met-127, Trp-127, Phe-127, Ile-127, Val-127; Ile-116 replacements: Arg-116, Lys-116, Asp-116, Gln-116, Asn-116, Glu-116, His-116, Ser-116, Thr-116, Pro-116, Tyr-116, Gly-116, Ala-116, Met-116, Trp-116, Phe-116, Val-116; Leu-121 replacements: Trp-121, Met-121, Ala-121, Gly-121, Tyr-121, Pro-121, Thr-121, Ser-121, His-121, Glu-121, Asn-121, Gln-121, Asp-121, Lys-121, Arg-121; Lys-112 replacements: Arg-112, Val-112, Ile-112, Phe-112, Tyr-112, Trp-112, Thr-112, Gly-112, Ser-112, Asp-112, Asn-112, Pro-112 and combinations of these replacements.

In addition it is anticipated that analogs of mammalian somatotropins that require harsher treatment to induce denaturation will aggregate to a lesser extent. This is because the amount of protein that forms the intermediate folded monomer is decreased relative to the native state. We and other have observed that human somatotropin requires significantly more denaturant for unfolding. The latter protein does not form a stable folding intermediate and does not precipitate as a result of this mechanism. Therefore, changing the primary structure of bSt sequence to match with the corresponding human sequence may lead to enhanced conformational stability and a decrease in the amount of aggregation observed. These include the following analogs containing one or more of the following substitutions: Ala-4→Thr; Met-5→Ile; Ser-6→Pro; Gly-9-→Arg; Ala-1-2→Asp; Val-15→Met; Gln-19→His; His-20→Arg; Ala-26→Phe; Phe-29→Tyr; Lys-30→Glnl; Arg-34→Glu; Thr-35→Ala; Glu-39→Lys; Gly-40→Glu; Arg-42→Lys; Ile-45→Leu; Thr-48→Pro; Val-50→Thr; Ala-51→Ser; Phe-52→Leu; Thr-57→Ser; Ala-60-→Thr; Thr-62→Ser; Gly-63→Asn; Lys-64→Arg; Asn-65→Glu; Ala-67→Thr; Asp-72→Asn; Gly-88→Glu; Leu-90→Val; Ser-94→Arg; Arg-95→Ser; Thr-98→Ala; Phe-103→Tyr; Thr-105→Ala; Arg-108→Ser; Ala-134→Thr; Leu-138→Phe; Asp-143→Ser; Met-149→Ser; Arg-150→His; Ser-151→Asn; Ser-163→Tyr; Leu-169→Met; His-170→Asp; Thr-172→Val; Lys-180→Gln; Phe-184→Ser; Gly-185→Val; Ala-187→Gly; Ala-190→Gly; insertion of Phe between residues 44 and 45; insertion of Asn between residues 108 and 109; deletion of Arg-182.

In addition, other structural changes are anticipated to generate enhanced structural stability. For example, enhancing the stability of α-helices spanning amino acid residues 7 to 34, 75 to 95, and 150 to 183, are likely to reduce aggregation. Enhancing the conformational stability of these helices can be accomplished, for example, by replacing amino acids of low α-helix forming potential with amino acids of higher α-helix forming potential with these regions. Examples of the latter approach include: Gly-9 Glu; Val-15→Leu; Asp-27→Glu; Phe-29→Leu; Ile-78→Leu; Phe-92→Leu; Ser-163→Gln; Arg-166→Lys; Thr-172→Glu; Tyr-175→Leu; Arg-177→Lys; Val-178→Leu.

BRIEF DESCRIPTION OF THE DRAWINGS

FIGS. 1A and B depict the amino acid sequence encoding bovine growth hormone.

DETAILED DESCRIPTION

A shorthand notation is used for denoting the various analogs of this invention. For example, Gln-121 refers to a somatotropin analog wherein glutamine is substituted for leucine at position 121, particularly of the bSt molecule as exemplified in FIG. 1B.

Due to the molecular heterogeneity of somatotropins, the numbering of amino acid residues within the various somatotropins may differ. The term "native mammalian somatotropin" includes these naturally occurring species. FIGS. 1A and B illustrate one of these native bSt species. The numbering for other somatotropins may differ where other species or other analogs are involved. Using the leucine 121 of the bSt set forth in FIG. 1B, those of ordinary skill in the art can readily locate corresponding amino acids in other animal somatotropins, for example, mammalian somatotropins, for example, leucine 121 of mammalian somatotropin, or their analogs, to achieve the desired decreased aggregation during processing (due to reduced hydrophobicity of helical stability) and enhanced bioactivity.

An apparent relationship exists between the aggregated folding intermediate of bSt (see discussion above) and the solubility of bSt in a variety of manufacturing conditions. Since an improvement in the solubility of bSt is desirable, analogs containing primary structure changes between residues 109–133, as exemplified herein, have been synthesized to create an improved bSt molecule. Analogs that are more soluble than native bSt may also lead to increased stability in the solid and solution states.

Both chemical and genetic modifications of the amino acid 109–133 region of bSt and other somatotropins are embraced by this invention.

The preferred genetic modifications have been synthesized by selective single site mutation methods for the replacement of the native amino acid sequence by other amino acid residues.

In preparing the analogs of this invention, the following factors are expected to decrease the stability of the α-helix normally found between residues 106 to 127 of the bSt primary sequence:

(i) Insertion of polar residues onto the hydrophobic face of the amphiphilic helix.

The hydrophobic face of this amphiphilic helix consists of the following residues: Tyr-110, Leu-113, Leu-116, Gly-117 (not hydrophobic but on the hydrophobic face) Ile-120, Leu-121, Leu-123, Met-124, and Leu-127. Porcine somatotropin does not contain a hydrophobic amino acid residue at position 121. Replacement of any of the hydrophobic residues (all but Glu-117) with any of the following amino acids is expected to reduce the ability of this region to drive α-helix formation through self-association: arginine, lysine, aspartic acid, glutamine, asparagine, glutamic acid, histidine, serine, threonine, and proline.

(ii) Insertion of amino acid residues near the $NH_2$ or $CO_2H$ terminal ends of the α-helix span residues 106 to 127, that destabilize this region of secondary structure due to repulsive interactions with the α-helix dipole.

The role of helix dipoles in stabilizing α-helix formation has been explored (Marcuse and Baldwin). For example, negatively charged amino acids (such as glutamic acid) placed near the carboxyl terminal of an α-helix help to destabilize α-helix formation. Therefore, replacement of Leu-127, or to a lesser extent, Arg-125 with aspartic acid or glutamic acid, or the replacement of residues 104 to 109 with lysine or arginine residues is expected to reduce α-helical stability. In particular, replacement of Asp-107 with a basic amino acid residue is expected to reduce helical stability.

(iii) The replacement of amino acid residues that have a strong propensity for α-helix formation, with amino acid residues that have lesser propensity for this type of secondary structure.

The listing below details the amino acid replacements which are expected to have decreased α-helical stability. These predictions are made on the basis of relative α-helical propensities as defined in Levitt, M. (1978) Biochemistry, 17, 4277–4285.

Ser-106→glycine or proline.

Val-109→threonine, tyrosine, glycine, serine, or proline.

Tyr-110→glycine or proline.

Glu-111, Glu-117, Glu-118, Glu-126→alanine, cysteine, leucine, glutamine, histidine, lysine, valine, isoleucine, phenylalanine, tyrosine, tryptophan, threonine, glycine, serine, aspartic acid, asparagine, proline, or arginine.

Lys-112, Lys-114→cysteine, valine, isoleucine, phenylalanine, tyrosine, tryptophan, threonine, glycine, serine, aspartic acid, asparagine, proline, or arginine.

Leu-113, Leu-116, Leu-121, Leu-123, Leu-127→alanine, cysteine, glutamine, histidine, lysine, valine, isoleucine, phenylalanine, tyrosine, tryptophan, threonine, glycine, serine, aspartic acid, asparagine, proline, or arginine.

Asp-107, Asp-115→valine, isoleucine, tyrosine, tryptophan, threonine, glycine, serine, asparagine, proline, or arginine.

Gly-119→proline.

Ile-120→valine, tyrosine, theonine, glycine, serine, asparagine, or proline.

Ala-122→cysteine, histidine, lysine, valine, isoleucine, phenylalanine, tyrosine, tryptophan, threonine, glycine, serine, aspartic acid, asparagine, proline, or arginine.

Met-124→any other naturally occurring amino acid residues.

Arg-108, Arg-125→valine, tyrosine, threonine, glycine, serine, asparagine, or proline.

Multiple replacements involving the foregoing are also contemplated. For example, a preferred embodiment has a glycine substituted for Arg-125 and a arginine substituted for Glu-126, and is designated Gly-125+Arg-126.

The phrase "animal somatotropin" refers to somatotropins originating from animals, e.g., mammals, and includes somatotropins derived from either natural sources, e.g., pituitary gland tissue or from microorganisms transformed by recombinant genetics to produce a naturally-occurring form of somatotropin. When a specific mammalian source is named such as bovine somatotropin or a somatotropin of bovine origin, the somatotropin includes those derived from either natural sources of from transformed microorganisms.

The term "microorganism" is used herein to include both single cellular prokaryotic and eukaryotic organisms such as bacteria, yeast, actinomycetes and single cells from higher plants and animals grown in cell culture.

The term "native" refers to naturally-occurring forms of somatotropins which may have been derived from either natural sources, e.g., pituitary gland tissue or from microorganisms transformed by recombinant genetics to produce a somatotropin having the same amino acid sequence as the naturally-occurring form of somatotropin.

The mammalian somatotropins are very similar in amino acid sequence and physical structure. Although the structural changes described in the Examples have been made within bSt, the processes are equally applicable to any animal, e.g., mammalian somatotropin having the requisite amino acid residues available for replacement, e.g., porcine somatotropin.

Relative potency of the bSt analogs of the present invention is readily determined using hypophysectomized rats. Evans, H. M. and Long J. A., Anat. Rec. 21:61, 1921, Relative increases in total body weight are recorded using pituitary bSt, rbSt and various bSt analogs of the invention.

Site-Directed Mutagenesis: Several techniques for site-directed mutagenesis have been developed for introducing specific changes in a DNA sequence and may be used to produce the compounds of the instant invention (Kramer, W., et al. Nucl. Acids Res. 12, pp. 9441–56 (1984); Mandecki, W., Proc. Natl. Acad. Sci. USA, 83, pp. 7177–81 (1986); Zoller, M. J. and Smith, M., Nucl. Acids Res., 10, pp. 6487–6500 (1982); Norrander, J., et. al., Gene, 26, pp. 101–106 (1983); Kunkel, T. A., Proc. Natl. Acad. Sci. USA, 82, pp. 488–92 (1985); Schold, A., et. al., DNA, 3, pp. 469–77 (1984) Marotti, K. M. and Tomich, C-S.C., Gene Anal. Tech. (In press). We employed the primer directed mutagenesis technique of Marotti and Tomich, using only primer for the mutagenesis reaction and gene 32 protein to increase mutagenesis efficiency.

Colony Filter Hybridization: The screening technique of filter hybridization is based upon the ability of a single-stranded segment of DNA to locate its complementary sequence and hybridize to form a double-stranded segment, Hanahan, D. and Meselson, M., Meth. Enzymol., 100, pp. 333–42 (1983). The thermal stability of this binding is dependent upon the number of matches and mismatches contained within the double stranded region. The more mismatches it contains, the weaker the base-pair binding and the lower the temperature necessary to disrupt the DNA binding. This temperature differential is exploited during colony filter hybridization, Bryan, R., et. al., Microbiology (1986). By constructing a mutant oligomer which maximizes the temperature differential between the native and mutant sequence, it is possible to hybridize at a lower temperature allowing binding of the probe to matched and nearly matched sequences. Upon washing at elevated temperatures, the mismatched probe-DNA duplex becomes unstable and disassociates while the perfectly matched duplex remains bound. The matched duplex will then produce the darkest signal on an autoradiogram thus forming a detection method for a colony containing the desired sequence. DNA from this colony can then be isolated and sequenced.

For filter preparation, nitrocellulose filters are overlayed onto the plates. The filters and plates are marked for orientation and the filters are then carefully lifted off the plates. The master plates are incubated overnight at room temperature to allow re-growth of the colonies. The filters are denatured by laying them one by one onto Whatman paper soaked in a 0.5M NaOH, 1.5M NaCl for 10 minutes and neutralized in two to three successive changes of Whatman paper soaked in 1M Tris, pH 7.4, 1.5M NaCl, for at least 10 minutes each and air dried on fresh Whatman paper for 30 minutes. They are then baked for 2 hours at 80° C. in vacuum.

The kinase reaction to radiolabel the oligonucleotide for use as a probe is as follows: 2 μg of oligonucleotide, 2 μl of 10X kinase buffer, 100 μCi α32-P ATP, 2 μl T4 kinase and water to a total volume of 20 μl are mixed and incubated for 1 hour at 37° C. A 1 ml column is packed with DEAE-Sephacel in a 10 ml disposable column and equilibrated with 2–3 ml of high salt buffer (1.5M NaCl in TE) and then 2–3 ml of low salt buffer (0.2M NaCl in TE). The kinase reaction is diluted with 200 μl of low salt buffer and loaded directly into the column. The column is washed with more than 5 ml of low salt buffer until no further counts elute from the column. The probe is eluted in 4–6 ml of high salt buffer.

To hybridize, the filters are placed in a crystallization dish and batch pre-hybridized in 5X Denhardts (1% BSA, 1% Ficoll and 1% PVP), 5X SSC (0.75M NaCl, 0.075M sodium citrate) and 0.1% SDS for 1–2 hours at 40° C. The hybridization solution is changed and the probe is added. The dish is covered and the hybridization done overnight with gentle agitation. The filters are then rinsed with several changes of 5X SSC, 0.1% SDS. The filters sit in this solution while the water bath and wash solution (5X SSC, 0.1% SDS) is heated up to appropriate washing temperature. The filters are transferred one by one to a fresh crystallization dish with wash solution and washed 3×20 minutes, changing dishes after each wash. They are then air dried on Whatman paper, wrapped in Saran wrap and exposed to X-ray film.

Vector DNA Preparation: DNA for sequencing is obtained according to the method described in Maniatis et al., Molecular Cloning: A Laboratory Manual. Cold Spring Harbor Laboratory, N.Y. (1982).

Sequencing: Double-stranded sequencing is performed according to the following protocol: 3 µl 2N NaOH, 2 mM EDTA is added to 12 µl of DNA (2 µg) and incubated for 15 minutes. 6 µl 3M NaOAc, 1 µl primer and 100 µl 95% ethanol are added and the DNA precipitated on dry ice for 20–30 minutes. The pellet is collected, washed and vacuum dried. It is dissolved in 13 µl water and 4 µl buffer (0.3M Tris-HCl, pH 8.3, 0.375M NaCl, 37.5 mM $MgCl_2$, 2.5 mM DTT), 2 µl (20 µCi) α32P dCTP and 1 µl reverse transcriptase are added. 4 µl of this mix is pipetted into 4 eppendorf tubes, each containing 1 µl of G mix, A mix, T mix or C mix. The tubes are incubated for 10 minutes at 42° C. 1 µl of chase mix (0.25 mM dNTPs) is added and they are incubated for an additional 5 minutes. 10 µl stop solution (80% formamide, 10 mM NaOH, 1 mM EDTA, 0.1% xylene cyanol and 0.1% bromphenol blue) is added, the reactions are boiled 3 minutes and 3 µl of each is loaded onto a sequencing gel.

Induction Protocol and SDS-PAGE Analysis: See PCT/US 88/00328.

Recombinant-DNA derived bSt was obtained from *E. coli* carrying a temperature sensitive runaway-replication-plasmid into which the appropriate gene sequence, along with a tryptophan promoter system, had been inserted, C-S.C. Tomich et al., Nucl. Acids Res. 17, pp. 3179–97 (1989). The fermentation and isolation of bSt was according to the procedure described by Evans and Knuth (Patent application WO 8700204).

Gln-121 bSt and Leu-112+Gln-121 bSt were obtained by oligonucleotide-directed mutagenesis on plasmid DNA according to the method of Marotti and Tomich, supra. The oligonucleotide with the sequence 5'GAAGGCATCCAG-GCTCTGATGC was used on the wild-type DNA sequence to generate Gln-121 bSt and on the Leu-112 DNA sequence to generate Leu-112+Gln-121 bSt. Mutants were detected by colony hybridization (Maniatis, T., Fritsch, et al., in Molecular Cloning, Cold Spring Harbor Laboratory, New York, 1982). The mutation was confirmed by sequencing the DNA by the chain termination method for double-stranded templates (Wallace, R. B., et al., Gene, 16, 21–26 (1982)). Transformation and plasmid preparations were according to that described by Maniatis, T., supra. The mutant bSt was obtained from the same strain of *E. coli* and isolated from the fermentation culture medium in an identical manner as for the wild-type recombinant-derived bSt.

Guanidine hydrochloride (Gdn HCl) was ultrapure from Schwartz/Mann. Other reagents were analytical grade.

bSt concentrations were determined by the absorbance at 278 nm using an extinction coefficient of 15.270 $M^{-1}$ (Burger, H. G., et al., J. Biol. Chem., 241, pp. 449–457 (1966)). Absorbance measurements were taken on an IBM 9420 spectrophotometer. CD measurements were obtained with a Jasco J-500 C spectropolarimeter. The results are reported as means residue ellipticity (MRE) in deg $cm^2$ $dmol^{-1}$ and were calculated using a mean residue weight of 115. Equilibrium denaturation, isoelectric focusing, kinetic studies, and reversed-phase HPLC results were obtained as previously described (Havel, H. A., et al., Biochemistry, 25, pp. 6533–6538 (1986); Brems, D. N., et al., Biochemistry, 25, pp. 6539–6543 (1986); Brems, D. N., J. Biol. Chem., 262, pp. 2590–2596; Brems, D. N., et al., Biochemistry, 24, pp. 7662–7668 (1985)). Tryptic mapping was according to Hartman, P. A., et al., J. Chromatogr., 360, pp. 385–395 (1986).

The two-step procedure for detection of the associated intermediate is as follows: in the first step, different concentrations of the associated intermediate are generated by dissolving varying concentrations of mutant or wild-type protein in 3.5M Gdn HCl, 8.5. After equilibration, aggregated protein is precipitated by dilution of the samples to 0.8M Gdn HCl and protein concentration of 0.18 mg/mL (8.2 µM). After 30 minutes the reaction mixture is added to a cuvette for turbidity measurements at 450 nm, or sedimented by centrifugation and filtered through a 0.45 µm filter. The remaining soluble protein content is determined by UV absorbance at 278 nm.

Apparent equilibrium constants for aggregate formation are calculated by using non-linear least squares curve fitting routines available in ASYST (MacMillan Software). Accurate determination of these constants are not dependent on using this software package. The calculated curves are determined by assuming a monomer-to-dimer equilibrium in which: $M+M \leftrightarrows D$; $K_{assoc.}=[D]/[M]^2$; and $[protein]_{total}=2[D]+[M]$, where [D] is the concentration of dimer; [M] is the concentration of monomer; and $K_{assoc.}$ is the association constant. To monitor association the protein concentration is varied, and a more negative MRE at 300 nm is assumed to be proportional to dimer formation. The calculated MRE= $MRE_M[M]+MRE_D[D]$, where $MRE_M$ is the mean residue ellipticity for monomer and $MRE_D$ is the mean residue ellipticity for dimer.

The kinetic data are analyzed by an On-Line Instrument Systems (OLIS, Jefferson, Ga.) 3920Z data acquisition and instrument control system. For this system the data are fit to a single exponential kinetic equation. The kinetic results are presented as time constants or $rate^{-1}$.

EXAMPLE 1

Production of Gln-121 bST

A site-directed mutagenic technique for double-stranded primer extension is used to introduce altered codons for glutamine at amino acid position 121 in the bSt cDNA m4 gene (PCT patent application PCT/US 88/00328, filed 27 Jan. 1988 and incorporated herein by reference). In this method, the target sequence is cloned into a suitable plasmid and plasmid DNA is prepared. The plasmid DNA is denatured by treatment with NaOH which causes "nicks" in the DNA molecule deoxyribose-phosphate backbone. This relaxes the DNA and permits an oligomer containing the desired sequence changes to hybridize to the plasmid sequence containing the position 121 residue of bSt. The 3' end of the oligomer generates a primer for the DNA polymerase activity of the reverse transcriptase which extends the primer, synthesizes a new DNA strand containing the mutagenic oligomer and displaces the normal complementary strand. The extension reaction increases the probability of the incorporation of the oligomer-directed change. The DNA is transformed into competent cells and the resultant colonies are screened by colony filter hybridization. Plasmid DNA is isolated and sequenced from positive candidates.

The oligomers used to construct the position 121 glutamine change in the bSt m4 gene are produced by techniques previously described (PCT/US 88/00328). An oligonucleotide so produced and set forth above contains the proper change.

EXAMPLE 2

Production of Leu-112+Gln-121 bSt

Following the techniques of Example 1, but substituting the appropriate oligomers encoding the desired amino acids, a bSt analog having leucine at position 112 and a glutamine at position 121 is also constructed.

EXAMPLE 3

Production of Gly-125+Arg-126 bSt

Following the techniques of Example 1, but substituting the appropriate oligomers encoding the desired amino acids, a bSt having a glycine at position 125 and an arginine at position 126 is also constructed.

EXAMPLE 4

Characterization of Gln-121 bSt, Leu-112+Gln-121, and Gly-125+Arg-126 bSt

Reversed-phase HPLC analysis of wild-type and bSt analog samples yields single chromatographic peaks. Substitution of lysine 112 with leucine causes a significant increase in retention time (about 8.5 minutes) while the change at position 121 causes a slight decrease in retention time (about 1.4 minutes) in the gradient system used. The double mutation at positions 112 and 121 causes an additive effect on the retention time.

Isoelectric focusing of wild-type and bSt analog samples gives the following pI values for the major component: 8.15 (wild-type), 7.0 (Leu-112), 8.25 (Gln-121), 7.05 (Leu-112+Gln-121), 8.7 (Gly-125+Arg-126). These values are consistent with the replacement of a (basic) lysine residue in wild-type bSt with a (neutral) leucine residue in Leu-112 bSt and Leu-112+Gln-121 bSt, as well as a net replacement of an (acidic) glutamic acid residue with glycine in the Gly-125+Arg-126 bSt analog.

Confirmation that the correct amino acid changes have been made in Gln-121 bSt, Leu-112+Gln-121, and Gly-125+Arg-126 bSt has been accomplished by peptide mapping of oxidized protein. The expected peptide fragments for mutants are missing from the map and new peaks are observed in the chromatograms which correspond to the peptides which have amino acids replaced. The changes in peptide retention times correlate with the changes in hydrophobicity of the peptide.

The new peaks which appear in the tryptic maps of the mutant proteins are also subjected to amino acid sequencing. For Gln-121 bSt, Leu-112+Gln-121, and Gly-125+Arg-126 bSt, the correct amino acid sequences are obtained.

A. At low protein concentration, Gln-121 bSt denatures like wild-type bSt but Leu-112 bSt and Leu-112+Gln-121 bSt denature like wild-type bSt at high protein concentration.

The equilibrium denaturation at low protein concentration of the wild-type and bSt analogs have been determined. For both Gln-121 and wild-type bSt the second derivative UV absorption and CD detected denaturation transitions are symmetrical and identical. However, for Leu-112 bSt and Leu-112+Gln-121 bSt, the CD detected transition is biphasic and the second-derivative UV absorbance detected transition is asymmetric. These types of transitions have been reported previously for the wild-type bSt at high concentration (Havel, H. A., et al., Biochemistry, 25, pp. 6533–6538 (1986), Brems, D. N., et al., Biochemistry, 25, pp. 6539–6543 (1986)). The biphasic and asymmetric denaturation transitions have been attributed to the presence of the associated intermediate (Havel, H. A., et al., supra; and Brems, D. N., et al., supra). The denaturation results show that at 0.04 mg/mL (1.8 µM) wild-type, Gln-121 and Gly-125+Arg-126 bSt do not show significant population of the associated intermediate, but Leu-112 bSt and Leu-112+Gln-121 bSt are associated. These results suggest that the association constant has been increased by substituting Lys-112 with Leu.

B. Gln-121 and Gly-125+Arg-126 bSt destabilize and Leu-112+Gln-121 bSt stabilizes the associated folding intermediate.

The CD at 300 nm measurement shows the population of associated intermediate for various bSt species goes in the following order:

Leu-112 bSt>Leu-112+Gln-121 bSt>wild-type bSt>Gln-121 bSt>Gly-125+Arg-126

At protein concentrations below 1 mg/mL (45 µM), the amount of associated species (as determined from a more negative ellipticity) in these proteins goes in the following order:

Leu-112 bSt>Leu-112+Gln-121 bSt>wild-type bSt>Gln-121 bSt>Gly-125+Arg-126 bSt

At concentrations above 2 mg/mL (91 µM), wild-type bSt has more negative ellipticity than Leu-112+Gln-121 bSt but less than Leu-112 bSt giving the following order for amount of associated species:

Leu-112 bSt>wild-type bSt>Leu-112+Gln-121 bSt>Gln-121 bSt>Gly-125+Arg-126 bSt

Concentration dependent effects demonstrate that changing Leu-121 to Gln decreases and changing Lys-112 to Leu increases the stability of the associated intermediate relative to wild-type bSt. In addition, replacing Arg-125 with glycine and Glu-126 with arginine decreases the stability of the associated intermediate relative to wild-type bSt. For Leu-112+Gln-121 bSt, the net effect on stability of the associated intermediate relative to wild-type bSt depends on the protein concentration.

C. Gln-121 bSt and Gly-125+Arg-126 bSt precipitate less and Leu-112+Gln-121 bSt precipitates more than wild-type bSt.

The associated intermediate is less soluble than the native or denatured conformations. This is demonstrated for the wild-type protein by a two-step procedure: 1) the associated intermediate is populated by adjusting solvent conditions for its maximal population and 2) the solvent conditions are changed to selectively precipitate the associated forms. This two-step procedure is utilized to compare the stability of the associated intermediate for the mutant and wild-type bSt's. The amount of precipitation for the various proteins goes in the following order:

Leu-112 bSt>Leu-112+Gln-121 bSt>wild-type bSt>Gln-121 bSt>Gly-125+Arg-126 bSt

The results demonstrate that there is approximately 36 and 72% less precipitate found with Gln-121 bSt and Gly-125+ Arg-126 bSt than wild-type bSt. The recovery of active bSt from transformed *E. coli* requires an in-vitro folding step. Since precipitation of the protein during folding would result in low recovery, Gln-121 bSt and Gly-125+Arg-126 bSt will result in higher yields of soluble active bSt from transformed *E. coli*.

D. At low protein concentration, Gln-121 bSt and Gly-125+Arg-126 bSt refold at the same rate as wild-type bSt but at high protein concentration they fold faster while Leu-112+Gln-121 bSt refolds slower.

The kinetics of bSt refolding are dependent on protein concentration with increasing concentration resulting in slower kinetics (Brems, D. N., et al., J. Biol. Chem., 262, pp. 2590–2596 (1987)). This concentration dependent effect is attributed to the presence of a transient associated intermediate that is identical or similar to that observed at equilibrium (Brems, D. N., et al., J. Biol. Chem., 262, 2590–2596 (1987). The presence of the associated intermediate during folding slows the rate because this intermediate does not lie directly on the path to the native state. The $N \rightleftarrows I$ reaction results in the observed UV absorbance change at 290 nm. Thus refolding as detected by UV absorbance at 290 nm would be rate-limited by the dissociation of $I_{assoc.}$. At low protein concentration (<0.3 mg/mL, 14 μM) (Gln-121 bSt refolds at the same rate as wild-type bSt (time constants of 72 sec and 75 sec, respectively) but Leu-112+Gln-121 bSt and Leu-112 bSt refold much slower (time constants of 113 and 130 minutes, respectively). At higher protein concentration appreciable amounts of the associated intermediate are populated for wild-type and Gln-121 bSt resulting in slower refolding. At low protein concentration (<0.3 mg/mL, 14 μM) wild-type Gln-121 bSt and Gly-125+Arg-126 bSt refold at the same rate but at higher protein concentrations (>0.5 mg/mL, 23 μM) Gln-121 bSt and Gly-125+Arg-126 refold faster than wild-type.

The hydrophobic face of this helix of rbSt is decreased by replacing Leu-121 with Gln and shifted by replacing Lys-112 and Leu-121 with Leu and Gln respectively. Gln-121 bSt decreased and Leu-112+Gln-121 bSt increased the stability of the associated intermediate. This modulation of the stability of the associated intermediate resulted in a decrease in the precipitation that occurs during refolding and an increase in the rate of refolding for Gln-121 bSt whereas Leu-112+Gln-121 bSt had the opposite effect. Alternatively, destabilization of the C-terminal portion of the helix found between residues 106 and 127 of the wild-type bSt by replacement of Arg-125 and Glu-126 with glycine and arginine, respectively, appears to occur. This indirectly increases the solubility of the latter protein since the hydrophobic interactions of this amphiphilic helix would involve fewer hydrophobic amino acid residues. These results indicate that bSt analogs with greater solubility and stability are made.

EXAMPLE 5

Activity of Gln-121 bSt and Leu-112+Gln-121 bSt

Activity of various position analogs was demonstrated. The parameter measured was to estimate differences in 3.5% fat corrected milk yield (FCM) of lactating dairy cows injected intramuscularly with native rbSt, the Gln-121 rbSt and the Leu-112 rbSt. Holstein cows (45) were ranked from high to low milk yield based on milk yield on days 3 and 2 prior to initiation of rbSt injections. The cows were assigned randomly in replicates, based upon milk yield, to experimental groups: no injection (Control), 5 mg and 15 mg Leu-112 daily, 5 mg and 15 mg Gln-121 daily, and 5 mg and 15 mg (clinical rbSt) daily. Cows were injected intramuscularly in the semitendinosus muscle once daily for 7 days. Twice daily milk weights were recorded for three days prior to initiation of injection, during the 7 days of injections, and for five days after the last injection. Concentration of rbSt was expected to be 10 mg/ml.

The concentration of residual post-injection rbSt solutions, measured colorimetrically, averaged 10.0 for clinical rbSt, 12.3 for Gln-121 rbSt and 11.8 for Leu-112 rbSt.

Statistical analysis of the FCM among experimental groups was based on average daily FCM for days 1 to 7 of injections using the three days prior to initiation of injections as the covariate.

Statistically significant effects were detected for rbSt Form (P=0.0004) and Dose (P=0.03); there was no statistically significant effect of interaction of rbSt Dose with rbSt Form (P=0.73). Average daily FCM for cows receiving Gln-121 rbSt (28.0 Kg) was slightly increased over cows receiving Clinical rbSt (26.8 Kg, P=0.08) and was significantly greater than that of cows receiving Leu-112 rbSt (25.5 Kg, P=0.0007), or non-injected Control cows (24.6, P=0.0002). A portion of the apparent increase in FCM of cows receiving Gln-121 rbSt compared to cows receiving Clinical rbSt was due to the greater dose of Gln-121 rbSt versus Clinical rbSt. The average daily FCM for cows receiving Clinical rbSt (26.8 Kg) appeared to be greater than that of cows receiving Leu-112 rbSt (25.5 Kg, P=0.063) and non-injected Controls (24.6 Kg, P=0.01). The average daily FCM for cows receiving Leu-112 rbSt (25.5 Kg) was not significantly different from that of Control cows (24.6 Kg, P=0.25, P=0.55). The slopes of the lines representing the FCM return to baseline after injection were not different indicating no detectable difference in rate of FCM decline among cows of the Experimental Groups. The result of reduced biological activity of Leu-112 rbSt is consistent with previous results of the rat growth assay and a previous lactating cow bioassay. Cows tolerated the daily injection and did not become fractious. No side effects as a result of administering rbSt or rbSt analogs were detected in these cows. Cows in the lots where rbSt injected cows resided consumed more feed that would be expected in the absence of rbSt injections.

EXAMPLE 6

Other Analogs

Following the teachings of the preceding examples with appropriate modifications, similar analogs to porcine, human, ovine, horse, rat, monkey and avian somatotropins may also be produced by replacing the appropriate amino acid residues (S. S. Abdel-Meguid, et al, Proc. Natl. Acad. Sci. USA, 84, pp. 6434–37 (1987)).

Administration of the bSt analogs into dairy cattle is according to known methods using any route effective to deliver the required dosage to the animal's circulatory system. Modes of administration include oral, intramuscular injections, subcutaneous injections and the use of timed-release implants. The preferred mode of administration is by subcutaneous injection using a timed-release implant. Appropriate vehicles for injections include physiologically compatible buffers such as sodium bicarbonate, sodium phosphate, or ammonium phosphate solutions. Timed-release implants are known in the art, e.g., U.S. Pat. No. 4,333,919.

The effective dosage range is from 1.0 to 200 milligrams per animal per day. The greater the amount of bSt given, the greater the resulting increase in growth, lactation or numbers of mammary parenchymal cells. Most preferably, the dosage range is from 5 to 50 milligrams per day.

Mammalian growth hormones are very similar in their amino acid sequences and hormones originating from one animal source can sometimes enhance the growth of the other unrelated species of animals (e.g., rats). For purposes of increasing growth rate of animals, the analogs of the present invention can be used to produced increased growth in the same species in which native bSt has been shown to have growth-related bioactivity such as bovines, sheep, rats, salmon and chickens. The preferred animals are bovines used for beef such as bulls, heifers or steers.

Beef cattle are slaughtered just prior to reaching full maturity and size. The bSt analogs of the instant invention can be used to produce increased growth rates in beef cattle by administration any time between weaning until slaughter. The bSts are administered to beef cattle for a minimum of 30 days and for a maximum of 450 days depending upon desired time of slaughter. Animals used for veal are typically slaughtered at approximately 6 months of age and 10 to 30 mg/day of the bSt analog is administered up until the age of slaughter to effectuate desired increases in growth rate.

For purposes of increasing lactation in bovines, particularly dairy cows, the bSt analog is administered between 30 and 90 days postpartum and continued for up to 300 days. The bSt analog will also increase lactation in other commercial milk-producing animals such as goats and sheep.

We claim:

1. A non-primate, mammalian somatotropin having substitutions in the amino acid residues corresponding to residues 106 to 127 of the amino acid sequence provided in FIG. 1B, which substitutions reduce the hydrophobicity or helical stability, and thereby the amount of aggregation, of said substituted non-primate, mammalian somatotropin as compared to said amino acid sequence provided in FIG. 1B, the substitution which is Gln-121.

2. A somatotropin according to claim 1 which is bovine somatotropin.

3. A somatotropin according to claim 1 which is porcine somatotropin.

4. A method for enhancing the growth of a non-primate, mammalian animal, which comprises administering to the animal a somatotropin according to claim 1.

5. The method of claim 4, wherein the animal is a bovine.

6. A method for increasing milk production in a cow, comprising administering to the cow a somatotropin according to claim 1.

7. A non-primate, mammalian somatotropin having substitutions in the amino acid residues corresponding to residues 106 to 127 of the amino acid sequence provided in FIG. 1B, which substitutions reduce the hydrophobicity or helical stability, and thereby the amount of aggregation, of said substituted non-primate, mammalian somatotropin as compared to said amino acid sequence provided in FIG. 1B, the substitution which is Gly-125+Arg-126.

8. A somatotropin according to claim 7 which is bovine somatotropin.

9. A somatotropin according to claim 7 which is porcine somatotropin.

10. A method for enhancing the growth of a non-primate, mammalian animal, which comprises administering to the animal a somatotropin according to claim 7.

11. The method of claim 10, wherein the animal is a bovine.

12. A method for increasing milk production in a cow, comprising administering to the cow a somatotropin according to claim 7.

* * * * *